(12) United States Patent
Eskilson (10) Patent No.: US 9,721,474 B2
(45) Date of Patent: Aug. 1, 2017

(54) METHOD, MEASURING DEVICE AND CONTROL UNIT FOR ADAPTATION OF VEHICLE CONVOY CONTROL

(71) Applicant: SCANIA CV AB, Södertälje (SE)

(72) Inventor: Anders Eskilson, Enskede gård (SE)

(73) Assignee: SCANIA CV AB (SE)

( * ) Notice: Subject to any disclaimer, the term of this patent is extended or adjusted under 35 U.S.C. 154(b) by 70 days.

(21) Appl. No.: 14/430,722

(22) PCT Filed: Sep. 19, 2013

(86) PCT No.: PCT/SE2013/051094
§ 371 (c)(1),
(2) Date: Mar. 24, 2015

(87) PCT Pub. No.: WO2014/046602
PCT Pub. Date: Mar. 27, 2014

(65) Prior Publication Data
US 2015/0243172 A1    Aug. 27, 2015

(30) Foreign Application Priority Data
Sep. 24, 2012    (SE) ........................................ 1251072

(51) Int. Cl.
*G05D 1/00*   (2006.01)
*G05D 3/00*   (2006.01)
(Continued)

(52) U.S. Cl.
CPC .................. *G08G 1/22* (2013.01); *A61B 5/18* (2013.01); *B60W 40/08* (2013.01); *H04L 67/12* (2013.01);
(Continued)

(58) Field of Classification Search
None
See application file for complete search history.

(56) References Cited

U.S. PATENT DOCUMENTS

| 5,781,119 A | 7/1998 | Yamashita et al. |
| 2002/0121981 A1* | 9/2002 | Munch .................. G08B 21/06 340/576 |

(Continued)

FOREIGN PATENT DOCUMENTS

| EP | 2 390 744 A1 | 11/2011 |
| WO | WO 2012/105889 A1 | 8/2012 |

OTHER PUBLICATIONS

International Search Report dated Feb. 7, 2014 issued in corresponding International patent application PCT/SE2013/051094.

(Continued)

*Primary Examiner* — Lail Kleinman
(74) *Attorney, Agent, or Firm* — Ostrolenk Faber LLP (57) ABSTRACT

A method (400), control device (240) and measuring unit (230) for adapting a control algorithm having at least one driver-dependent parameter, which control algorithm governs the control of a vehicle convoy (200) in which at least a first vehicle 220A with a first driver (210A) and a second vehicle 220B with a second driver (210B) are included. The method includes measurement (401) of at least one physical characteristic of the first driver (210A), determination (402) of the stress level of the driver based on the performed measurement (401), and adaptation (403) of the control algorithm to the determined (402) stress level of the driver.

26 Claims, 6 Drawing Sheets

(51) Int. Cl.
*G06F 7/00* (2006.01)
*G06F 17/00* (2006.01)
*G08G 1/00* (2006.01)
*A61B 5/18* (2006.01)
*B60W 40/08* (2012.01)
*H04L 29/08* (2006.01)
*G08G 1/16* (2006.01)
*A61B 5/01* (2006.01)
*A61B 5/021* (2006.01)
*A61B 5/024* (2006.01)
*A61B 5/053* (2006.01)
*A61B 5/08* (2006.01)
*A61B 5/11* (2006.01)
*A61B 5/145* (2006.01)
*A61B 5/00* (2006.01)

(52) U.S. Cl.
CPC .............. *A61B 5/01* (2013.01); *A61B 5/021* (2013.01); *A61B 5/024* (2013.01); *A61B 5/0533* (2013.01); *A61B 5/0816* (2013.01); *A61B 5/11* (2013.01); *A61B 5/14546* (2013.01); *A61B 5/4266* (2013.01); *B60W 2040/0872* (2013.01); *B60W 2540/22* (2013.01); *G08G 1/16* (2013.01)

(56) References Cited

U.S. PATENT DOCUMENTS

| | | | |
|---|---|---|---|
| 2003/0146841 A1* | 8/2003 | Koenig | A61B 5/18 340/576 |
| 2011/0224844 A1 | 9/2011 | Farwell et al. | |
| 2011/0224875 A1 | 9/2011 | Cuddihy et al. | |
| 2015/0091740 A1* | 4/2015 | Bai | G08B 21/06 340/901 |

OTHER PUBLICATIONS

International Preliminary Report on Patentability dated Jan. 20, 2015 issued in corresponding International patent application PCT/SE2013/051094.

* cited by examiner

METHOD, MEASURING DEVICE AND CONTROL UNIT FOR ADAPTATION OF VEHICLE CONVOY CONTROL

CROSS-REFERENCE TO RELATED APPLICATIONS

The present application is a 371 national phase of International Application no. PCT/SE2013/051094, filed Sep. 19, 2013 which claims benefit of Swedish patent application no. 1251072-3, filed Sep. 24, 2012, the contents of which are incorporated herein by reference.

TECHNICAL FIELD OF THE INVENTION

The invention concerns a method, a measuring device and a control unit in a vehicle that is included in a vehicle convoy. More specifically the invention describes a mechanism for adapting a control algorithm that governs a vehicle convoy to a stress level of the vehicle driver.

BACKGROUND

For all control systems in a vehicle with which the vehicle driver interacts, it is fundamental to attempt to carry out what the driver requests in a manner that it is believed the driver desires. Vehicle refers in this context to, for example, a goods vehicle, semi, platform truck, carrier vehicle, truck, motor home, pickup, van, personal vehicle, emergency vehicle, watercraft, minivan, four-wheeler, scooter, excavator, car, crane truck, tanker truck, motorcycle, wheel loader, moped, scooter, limousine, sports car, racing car, bumper car, dragster, ride-on lawnmower, tank, snowmobile, snowcat, all-terrain vehicle, tracked vehicle, tractor, go-cart, bus, combine harvester, agricultural machine or similarly motor-driven manned or unmanned mode of conveyance, adapted for land-based geographical movement.

Platooning is a collective term for methods in which one has a plurality of vehicles on a road drive in locked groups with minimal or reduced distances between the vehicles in order to reduce fuel consumption and increase the transport capacity of the highway system.

Vehicles in the vehicle convoy can be connected to one another by means of electronic systems that communicate via radio links between the vehicles and the outside world, although various types of mechanical links between the vehicles are also conceivable. A synchronized vehicle convoy moves as a unit wherein the driver of one of the vehicles, normally the driver in the first vehicle, sets the pace for the entire convoy. The distance between the vehicles can be determined by means of sensors that are based on, for example, radar. The vehicles that are included in the vehicle convoy can thereby accelerate and/or brake simultaneously while still maintaining the same distance between the included vehicles.

Individual vehicles with platooning support can join or leave the vehicle convoy whenever so necessitated by their individual transport tasks.

Lower fuel consumption is achieved hereby in that the vehicles that are following the first vehicle encounter reduced air resistance. Reduced fuel consumption leads in turn to lower shipping costs and reduced environmental emissions. Yet another advantage is that it is possible to increase the capacity of the highway system by packing the vehicles more tightly together in the coordinated vehicle convoys while maintaining or possibly even increasing traffic safety. Increased transport capacity can contribute to reduced traffic backups and thus shorter transport times.

Additional advantages of vehicle convoys can consist in that new operating mechanisms can be applied, such as electrical driving by means of wires, guide tracks in the roadway or the like.

One problem with platooning is that the lead vehicle of the vehicle convoy with its driver is assigned a decisive function in leading the convoy in a safe manner. If, for any reason, this driver experiences panic, heavy stress, sudden illness or is unable for some other biological reason to perform his duties as the leader, the consequence can be that the safety of the entire vehicle convoy and its surroundings will be threatened.

Yet another problem is that even though platooning does not, in theory, require the vehicle drivers other than the leader of the vehicle convoy to be active, there is a moment when the automation is coupled in and out as the individual vehicle joins or leaves the vehicle convoy. Manual activity can be required on the part of the driver of the affected vehicle at such moments, which can threaten the safety of the entire vehicle convoy. In panic situations, the drivers in each individual vehicle can thus also threaten the safety of the vehicle convoy and its surroundings as they join or leave the vehicle convoy.

Figure 1A:
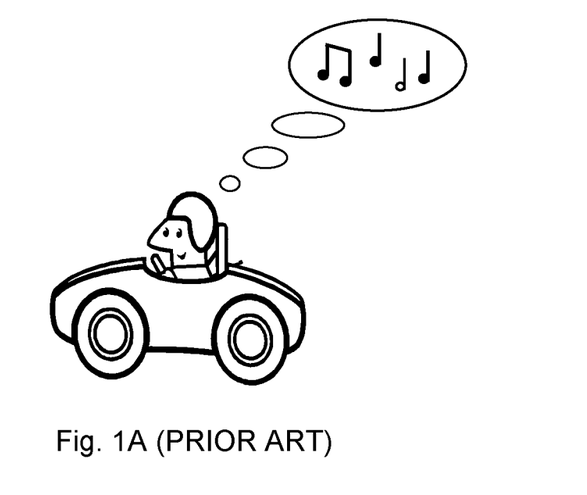
FIG. 1A is an illustration of a harmonious and rational vehicle driver.

Furthermore, certain control systems for vehicle convoys are adapted so as to be regulated by the lead vehicle by interpreting the regulating adjustments made by the driver in terms of, for example, velocity or acceleration, including by reading the speed with which the driver changes the position of the gas pedal and/or the position of the brake pedal in different directions in order to gain an idea of the behavior that the driver desires of the vehicle convoy. This generally works well as long as the driver in the lead vehicle is in a harmonious state and/or is acting rationally; see FIG. 1A.

Figure 1B:
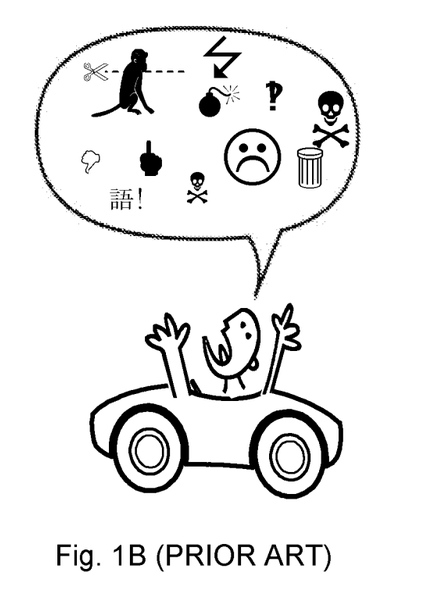
FIG. 1B is an illustration of a disharmonious and irrational vehicle driver.

However, one problem with the aforedescribed vehicle convoy is its heavy dependency on appropriate behavior on the part of the lead vehicle of the convoy and its driver. A driver in a traffic environment is unfortunately often subjected to stressful traffic situations and does not always behave rationally; see FIG. 1B. For example, the driver can be stuck in a backup in rush hour traffic, while at the same time having an appointment to keep, or be affected emotionally by perceived or actual deficiencies in the driving by other drivers of their respective vehicles, which can trigger at least temporary irrational driver behavior.

Control systems for vehicle convoys are adapted for rational behavior by the drivers in the vehicles that are included in the vehicle convoy. As a result, the vehicle convoy may behave irrationally if/when the lead driver behaves irrationally, which can threaten the safety of all the vehicles in the vehicle convoy as well as that of other drivers on the road.

It is likely that a driver who is troubled by stress, irritation, anger and/or frustration (see FIG. 1B) may amplify the signals that the control system for the vehicle convoy is attempting to interpret, for example by rapidly switching between full depression of the gas pedal and no depression at all, and then full depression again. Such gas pedal fluctuations can, as a result of interpretation problems and possible time delays, cause the control system to react in opposition to what the driver actually wants, i.e. that the clutch may release when the driver actually wants to drive forward and/or vice versa. The result can be that the vehicles in the vehicle convoy lose pulling force when the driver in the lead vehicle actually wants to increase the pulling force in the stressful situation. This behavior can further result in increased fuel consumption and thus increased environmental impact, but it can also result in increased wear to the vehicles included in the vehicle convoy or components thereof, such as the clutch and/or driveshaft, unnecessary/superfluous gear shifting, or an accident.

It can be shown that drivers, and perhaps in particular professional drivers, are often subjected to situational stress. A driver of a lead vehicle in a vehicle convoy who is driving irrationally risks causing damage to the vehicle, other vehicles in the vehicle convoy and/or other drivers on the road, above and beyond the potential personal suffering that may result.

SUMMARY

One of the objects of this invention is consequently to be able to adapt a control algorithm that is governing a vehicle convoy to a stress level of the driver of a vehicle that is included in the vehicle convoy in order to solve at least one of the aforementioned problems and thereby achieve a vehicle improvement.

According to a first aspect of the invention, this object is achieved by means of a method for adapting a control algorithm comprising at least one driver-dependent parameter, which control algorithm governs the control of a vehicle convoy. The vehicle convoy includes at least a first vehicle with a first driver and a second vehicle with a second driver. The method comprises a measurement of at least one physical characteristic of the first driver. The stress level of the first driver is determined based on this performed measurement. The control algorithm can subsequently be adapted to the determined stress level of the first driver.

According to a second aspect of the invention, this object is achieved by means of a control unit for governing a vehicle convoy by means of an adaptable control algorithm. The vehicle convoy includes at least a first vehicle with a first driver and a second vehicle with a second driver. The control unit comprises a communication module for receiving a measurement result from a measurement of at least one physical characteristic of the first driver. The control unit also comprises a processor circuit arranged so as to determine the stress level of the first driver based on the performed measurement, and further arranged so as to adapt the control algorithm to the determined stress level of the first driver.

According to a third aspect of the invention, this object is achieved by means of a measuring device for supplying measurement results for adapting a control algorithm that comprises at least one driver-dependent parameter, wherein the control algorithm governs a vehicle convoy. The vehicle convoy includes at least a first vehicle with a first driver and a second vehicle with a second driver. The measuring device comprises a detector for measuring at least one physical characteristic of the first driver. The measuring device further comprises a communication module for communicating the measured value to a control unit.

An elevated stress level on the part of the driver can be detected by measuring at least one physical stress-related parameter of at least one driver of one vehicle in a vehicle convoy, and by being able to detect an elevated stress level on the part of said driver by comparing said stress-related parameter to a limit value. The detected stress can then trigger an adaptation of the control algorithm that is governing the vehicle convoy to the elevated stress level of the driver. Excessive driver input can thereby be filtered out, suppressed and/or time shifted, and vehicle distances and velocities within the vehicle convoy can be regulated in order to achieve gentler and/or safer control of the vehicle convoy. The safety of the forward travel of the vehicle convoy can thus be increased, whereupon the risk of accident for the vehicles in the vehicle convoy and its drivers is reduced. An improvement in the control of the vehicle convoy is thereby achieved.

Other advantages and additional new features will be presented in the following detailed description of the invention.

BRIEF DESCRIPTION OF THE DRAWINGS

The invention will now be described in further detail with reference to the accompanying figures, which illustrate embodiments of the invention.

DESCRIPTION OF EMBODIMENTS

The invention is defined as a method, a control unit and a measuring device, which can be realized in any of the embodiments described below. However, this invention can also be realized in many different forms, and must not be viewed as being limited by the embodiments described herein, which are rather intended to elucidate and clarify various aspects of the invention.

Additional aspects and features of the invention may be identified in the following detailed description when it is viewed in conjunction with the accompanying figures. However, the figures are to be viewed only as examples of various embodiments of the invention, and must not be seen as limiting the invention, which is limited solely by the accompanying claims. Furthermore, the figures are not necessarily drawn to scale and are, unless otherwise specified, intended to illustrate aspects of the invention conceptually.

Figure 2A:
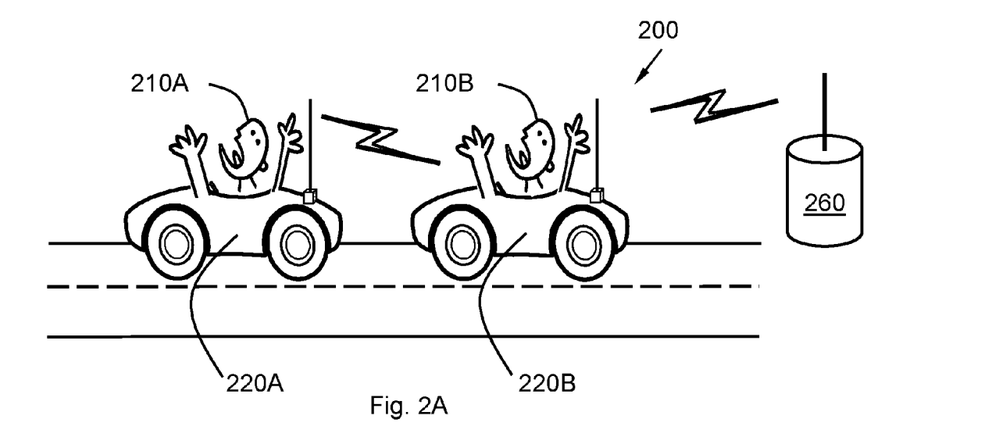
FIG. 2A is a general illustration that shows on embodiment of the invention.

FIG. 2A shows a vehicle convoy 200 that is controlled by a control algorithm. The vehicle convoy 200 includes a first vehicle 220A that is driven by a first driver 210A, and a second vehicle 220B that is driven by a second driver 210B. These vehicles 220A, 220B that are included in the vehicle convoy 200 are controlled by the driver 210A of the first vehicle. Furthermore, the vehicles 220A, 220B that are included in the vehicle convoy 200 are adapted so as to communicate wirelessly with one another.

Figure 2B:
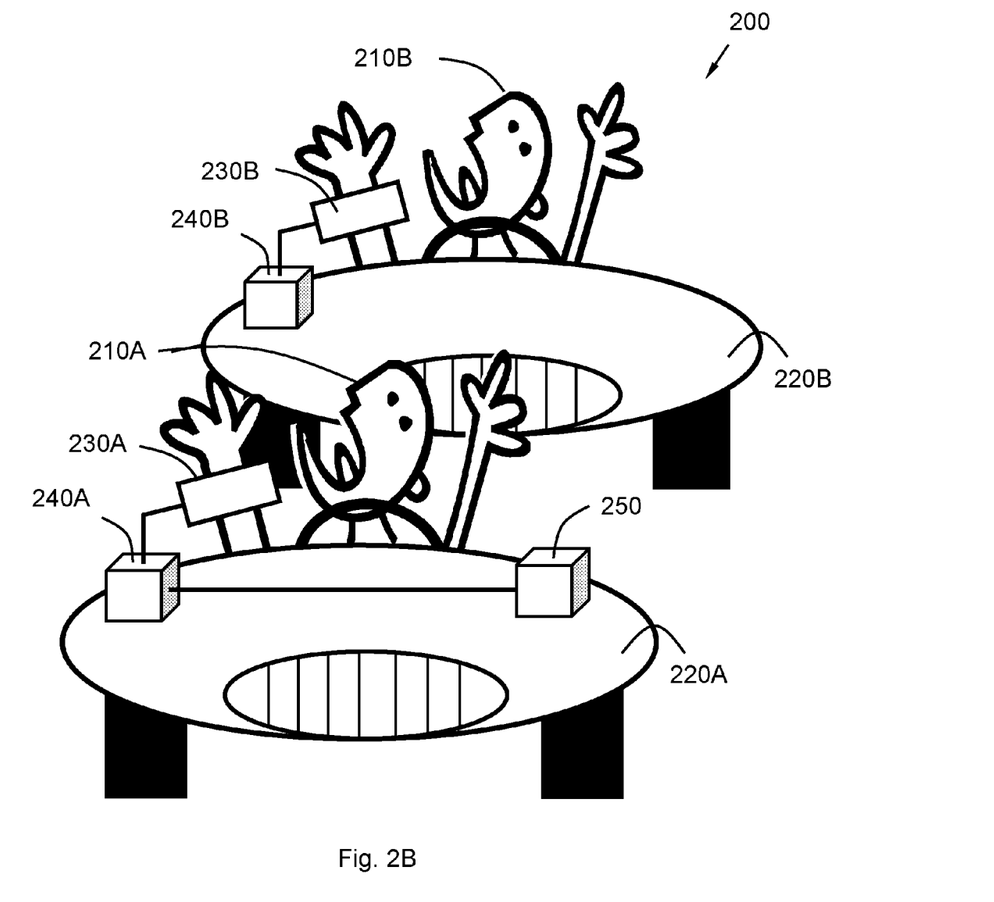
FIG. 2B is a general illustration that shows one embodiment of the invention.

FIG. 2B shows a vehicle convoy 200, which is identical, nearly identical or similar to the vehicle convoy 200 that is clarified in FIG. 2A.

A first measuring device 230A is adapted so as to scan one one or certain physical parameters of the driver 210A of the first vehicle. A second measuring device 230B is adapted so as to scan one or certain physical parameters of the driver 210B of the second vehicle, such as blood pressure and/or pulse. Each respective measuring device 230A, 230B then transmits these measurement values to a corresponding first and/or second control unit 240A, 240B over a wireless or wired connection. The control unit 240A, 240B in turn acts upon the control system 250 of the vehicle convoy. An external storage unit 260 is further adapted so as to receive and store the measurement values that the respective measuring devices 230A, 230B register for the driver 210A of the first vehicle and/or the driver 210B of the second vehicle.

The measuring device 230A, 230B is arranged so as to measure one or several of the following physical parameters of the drivers 210A, 210B, for example systolic blood pressure, diastolic blood pressure, pulse, cardiac minute volume, vascular resistance, respiratory volume, respiratory rate, body temperature, skin temperature, blood adrenalin level, blood cortisol level, blood noradrenalin level, transpiration volume, amount of hand sweat exuded, electrical conductivity of the skin, eye movement, dilated nostrils, muscular tension, body movement, speech volume, voice strength and/or pupil size of the driver 210A, 210B. The system can further comprise a plurality of separate measuring devices 230A, 230B in certain embodiments.

In certain embodiments the measuring device 230A, 230B is arranged so as to worn around the wrist by the driver 210A, 210B. According to other embodiments the measuring device 230A, 230B is connectable to another part of the body of the respective driver 210A, 210B such as, for example, the finger, hand, arm, neck, part of the head, skin, torso, rectum, leg or foot. According to further embodiments the measuring device 230A, 230B consists of a plurality of separate measuring devices, each of which measures various physical parameters on the driver 210A, 210B and sends them to the control device 240A, 240B and/or the control system 250 of the vehicle convoy. The measuring device 230A, 230B, or the measuring devices can also, in certain alternative embodiments, be arranged so as to detect and measure physical parameters of the driver 210A, 210B remotely, and can be secured, for example, in the cab and/or the driver seat. The term measuring device 230A, 230B can thus also encompass a plurality of separate measuring devices disposed in the same or separate locations on the respective driver 210A, 210B, in proximity to the driver, in the cab or at a certain distance from the respective driver 210A, 210B in different embodiments. To name just one example, a measuring device 230A, 230B that is adapted so as to measure the skin temperature of the driver can comprise a temperature sensor connected to the skin of the driver in one embodiment, but alternatively can instead comprise an infrared camera adapted so as to measure the skin temperature of the driver and disposed at a distance from the driver 210A, 210B, for example in the cab.

The measuring device 230A, 230B is further arranged so as to communicate with a control unit 240A, 240B and/or the control system 250 of the vehicle convoy via an interface, which can consist of a wireless interface in certain embodiments, but can also consist of a wired interface. The wireless interface can consist of a radio transmitter based on wireless communication technology such as 3rd Generation Partnership Project (3GPP) Long Term Evolution (LTE), LTE-Advanced, Evolved Universal Terrestrial Radio Access Network (E-UTRAN), Universal Mobile Telecommunications System (UMTS), Global System for Mobile Communications/Enhanced Data rate for GSM Evolution (GSM/EDGE), Wideband Code Division Multiple Access (WCDMA), World-Wide Interoperability for Microwave Access (WiMax), Wireless Local Area Network (WLAN) Ultra Mobile Broadband (UMB), Bluetooth (BT) or an infrared transmitter, to name just a few conceivable examples of wireless communication.

In certain embodiments the measuring device 230A, 230B is arranged so as to communicate one or some of the measured physical parameters of the driver 210A, 210B to the control unit 240A, 240B via a communication bus. Such a communication bus is arranged so as to couple a number of electronic control units (ECUs), or controllers, and various components arranged on the vehicle 220A, 220B together.

The control unit 240A, 240B is in turn arranged so as both to communicate with the measuring device 230A, 230B, in order to receive the measurement values, and optionally also trigger a measurement, for example at a given time interval. The control unit 240A, 240B is further arranged so as to communicate with the control system 250 of the vehicle convoy, for example via at least the communication bus of the relevant vehicle, which can consist of one or a plurality of a cable; a data bus, such as a CAN bus (Controller Area Network bus), a MOST bus (Media Oriented Systems Transport), or any other bus configuration; or of a wireless connection according, for example, to any of the previously enumerated technologies.

In certain embodiments the control unit 240A, 240B can further be integrated with the control system 250 of the vehicle convoy.

In certain embodiments the control unit 240A, 240B is arranged so as to forward the measurement values registered for the driver 210A, 210B by the respective measuring device to an external storage unit 260 over a wireless interface according to, for example, any of the previously enumerated wireless communication technologies.

The external storage unit 260 is further adapted so as to receive and store these measurement values, which can then be analyzed. A degraded health condition on the part of an individual driver 210A, 210B can thereby be detected, and an appropriate health-promoting package of measures can be assigned to the driver 210A, 210B with a view to disrupting his negative health trend and preventing disease, sick-listing and/or accidents, and encouraging a more positive lifestyle. For example, in certain embodiments, abuse of stimulants or performance-enhancing drugs by the driver 210A, 210B can be detected. The stored measurement values can also be used, for example, to investigate accidents that have occurred, and may enable detection of whatever physical parameter or parametric changes preceded an accident. Such detection can be used to further improve the control algorithm for the control system 250 of the vehicle convoy, as well as other control algorithms for, for example, the vehicle brake system or the like.

The control system 250 of the vehicle convoy is arranged so as to affect and control, for example, the distance between the vehicles 220A, 220B that are included in the vehicle convoy 200, the velocity of the vehicles 220A, 220B, the acceleration of the vehicles 220A, 220B that are included in the vehicle convoy 200, and similar parameters.

The control algorithm that governs the control system of the vehicle convoy 250 is affected by one or a plurality of parameters, which can be driver-dependent, indirectly driver-dependent or driver-independent such as, for example, the inclination of the vehicle, vehicle weight, vehicle type, driving comfort, selected performance, vehicle velocity and/or engine rpm.

Aggressive or irrational behavior on the part of the driver 210A of the lead vehicle can be detected by means of the embodiments described herein, and their consequences for the control system 250 and the vehicles 220A, 220B can be reduced. But a health condition that is hazardous for vehicle traffic, such as a circulatory disorder, blood pressure drop, fainting, heart attack, stroke, epileptic attack or the like can also be detected and/or predicted, and its consequences for the control system 250, the vehicle convoy 200 and the included vehicles 220A, 220B can be reduced.

Figure 3:
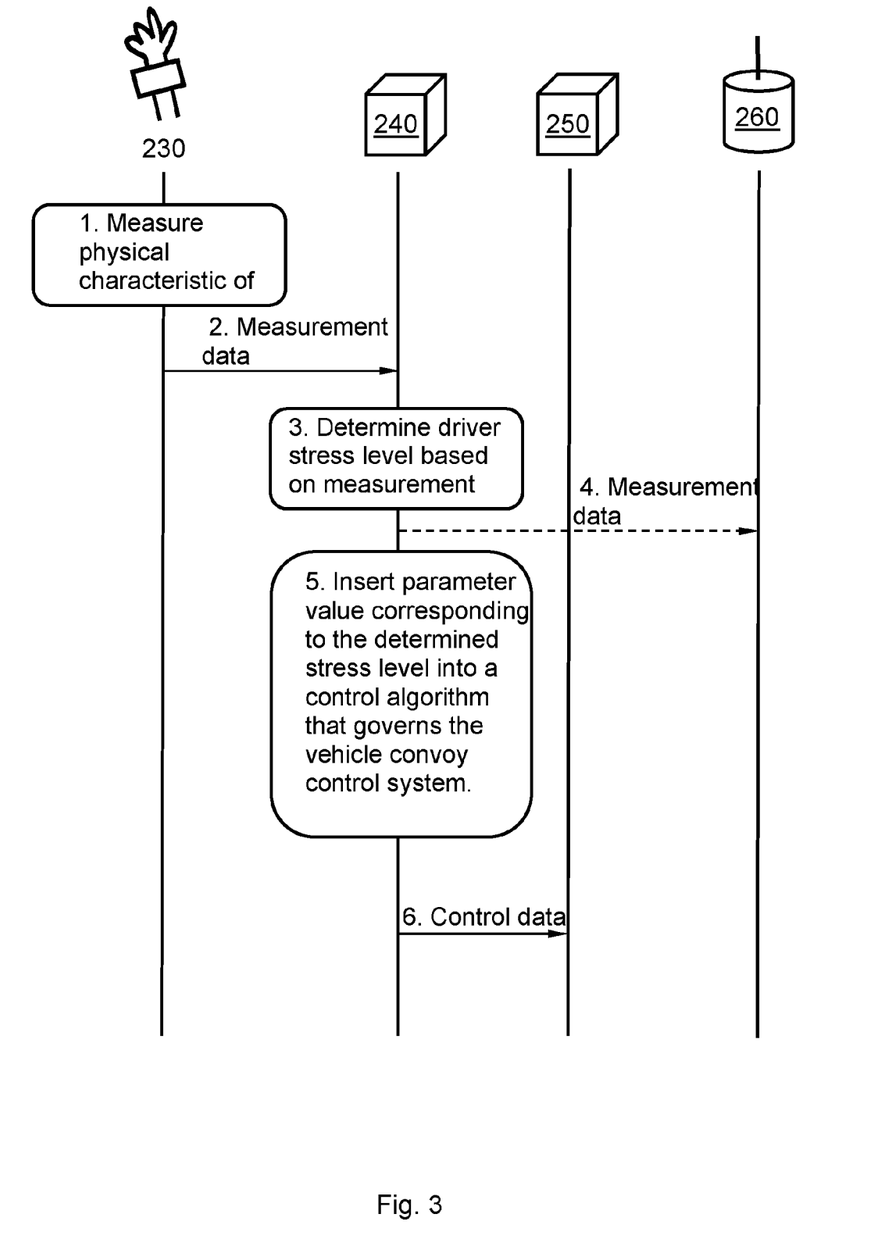
FIG. 3 is a combined flow and block diagram that shows one embodiment of the invention.

FIG. 3 clarifies a general example of the invention, divided into a number of steps 1-6. Note that certain of these stops are not necessarily included in all embodiments of the invention. Furthermore, these steps can be performed in a order other than that indicated by the numbering in certain embodiments. Certain steps can optionally also be performed in parallel with one another.

Step 1

The measuring device 230A, 230B measures a physical characteristic of at least the first driver 210A. This physical characteristic can consist of, for example, blood pressure or pulse.

Step 2

This measured physical characteristic is sent to the control unit 240A by means of wireless or wired signaling, for example via the communication bus of the vehicle.

Step 3

The control unit 240A receives the measurement values for at least one physical characteristic of the driver 210A. This measurement value is used to determine the stress level of the driver by, for example, comparing the received value to a limit value, by detecting the magnitude of a change between the two measured values, and/or by detecting the rate of change between two measured values.

Step 4

In certain embodiments the received measurement values are forwarded from the control unit 240A to an external data storage unit 260 in order to enable, for example, a health analysis of the driver 210A.

Step 5

The control unit 240A is arranged so as to adapt a control algorithm comprising at least one driver-dependent parameter, which control algorithm adapts the control system 250 of the vehicle convoy to the determined stress level of the driver.

This adaptation of the control algorithm can include performing filtering to eliminate the movement of the gas pedal, or of another driver-dependent parameter, and/or time filtering of the request for a shift of gears by the driver, with a view to achieving gentler power transfer in certain embodiments.

In certain embodiments the control algorithm is adapted to the determined stress level of the driver in that a suppression of a driver-dependent parameter is introduced that is in proportion to the stress level of the driver.

One advantage that is achieved thereby is that the vehicle convoy 200 will be subjected to more uniform velocity, acceleration, gear shifting etc, regardless of the mental state of the first driver (calm/agitated). Stress-related differences in driving behavior between different lead drivers 210A for the vehicle convoy 200 are thereby neutralized, which enables greater predictability of the behavior of the vehicle convoy for other drivers 210B in the vehicle convoy 200, and for other drivers on the road, which can have an accident-reducing effect in and of itself.

Step 6

Control data, corrected and adapted to the stress level of the first driver, are then sent to the control system 250 of the vehicle convoy so as, by means thereof, to affect and guide decisions regarding the maneuvering, velocity regulation, gear shifting, vehicle spacing and the like of the vehicle convoy.

Figure 4:
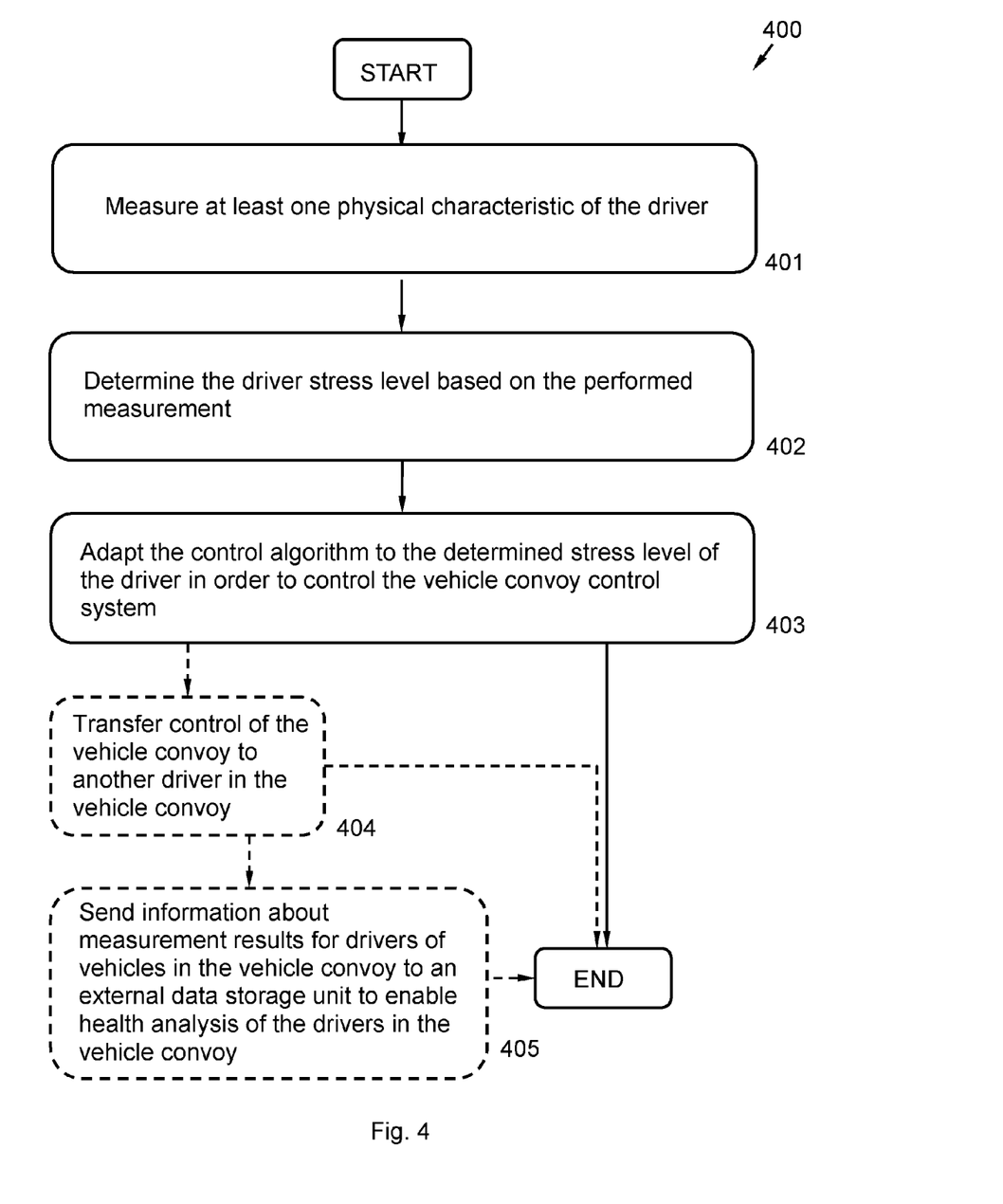
FIG. 4 is a flow diagram that illustrates one embodiment of a method for adapting a control algorithm.

FIG. 4 illustrates one example of an embodiment of the invention. The flow diagram in FIG. 4 clarifies a method 400 for adapting a control algorithm comprising at least one driver-dependent parameter, which control algorithm governs the control of a vehicle convoy 200 in which at least a first vehicle 220A with a first driver 210A and a second vehicle 220B with a second driver 210B are included.

The control algorithm can, in certain embodiments, comprise at least one driver-dependent parameter from among: the inclination of a gas pedal, inclination of a shift pedal, inclination of a brake pedal, change in inclination of the gas pedal, change in inclination of the shift pedal, change in inclination of the brake pedal, change in inclination of the gas pedal per unit of time, change in inclination of the shift pedal per unit of time, change in inclination of the brake pedal per unit of time, steering wheel deflection and/or rate of change of steering wheel deflection. Furthermore, the control algorithm in certain embodiments can comprise at least one driver-independent parameter from among: vehicle type, inclination of the vehicle 220a, 220B, vehicle weight, comfort level, engine rpm. In certain configurations the parameter comfort level can be adjustable by the driver 210A, 210B, the vehicle owner, the vehicle manufacturer or another actor.

The object of the method is to adapt the control algorithm to the elevated stress level of the driver, whereby the parameters that are not directly driver-dependent are given greater proportional weight compared to directly driver-dependent parameters.

To be able to adapt the control algorithm in a correct manner, the method 400 can comprise a number of method steps 401-405. However, it should be noted that some of the steps described here are included only in certain alternative embodiments of the invention, such as, for example step 404 and/or 405. It may also be noted that the steps described here can be performed in a somewhat different chronological order than that indicated by the numbering, and that some of them can be performed in parallel with one another. The method 400 comprises the following method steps:

Step 401

A measurement is made of at least one physical characteristic of the first driver 210A. This measurement can be made by one or a plurality of measuring devices 230A.

In certain embodiments, a measurement is made of at least one physical characteristic of a plurality of drivers 210A, 210B in the vehicle convoy 200. This measurement can be made by one or a plurality of measuring devices 230A, 230B.

The measurement of the physical characteristic of the driver 210A, 210B can be made by the measuring device 230A, 230B which, for example, can designed as a cuff that is connectable to the arm of the driver or another body part of the driver 210A, 210B in certain embodiments, such as, for example, a finger, hand, arm, neck, part of the head, skin, torso, rectum, bone or foot. According to additional embodiments, the measuring device 230A consists of a plurality of separate measuring devices, each of which measures different physical parameters of the driver 210A, 210B and sends them to the control device 240A, 240B. The measuring device 230A, 230B, or the measuring devices, can also, in certain embodiments, be arranged so as to detect and measure physical parameters of the driver 210A, 210B remotely, and can be secured in, for example, the cab and/or driver seat. The term measuring device 230A, 230B can thus also encompass a plurality of separate measuring devices disposed in the same or separate locations on the driver 210A, 210B, in proximity to the driver, in the cab or at a certain distance from the driver 210A, 210B in different embodiments. The measured physical characteristics of the driver 210A, 210B can be sent wirelessly or via cable to a control unit 240A, 240B.

However, the measuring device 230A, 230B can consist of a plurality of measuring devices, or of one measuring device 230A, 230B comprising a number of different detectors, which can have the same or different special locations.

In one embodiment, the measuring device 230A, 230B can comprise or partly comprise the horn of the vehicle, as the emotionally agitated driver 210A, 210B will likely have a tendency to overuse the horn.

The measured physical characteristics of the driver 210A, 210B can further comprise any of: systolic blood pressure, diastolic blood pressure, pulse, cardiac minute volume, vascular resistance, respiratory volume, respiratory rate, body temperature, skin temperature, blood adrenalin level, blood cortisol level, blood noradrenalin level, transpiration volume, amount of hand sweat exuded, electrical conductivity of the skin, eye movement, dilated nostrils, muscular tension, body movement, speech volume, voice strength and/or pupil size of the driver 210A, 210B according to certain embodiments.

The measured 401 physical characteristic of the driver 210A, 210B can, in certain embodiments, comprise a level change in at least one measured physical characteristic of the driver 210A, 210B.

In certain embodiments the measured physical characteristic of the driver 210A, 210B comprises a level change per unit of time in at least one measured physical characteristic of the driver 210A, 210B.

In certain embodiments only one individual physical driver characteristic is measured, which results in a rapid and simple analysis and a lower price for the measuring device 230A, 230B. In addition, only a limited amount of data needs to be transmitted to the control unit 240A, 240B and processed and analyzed therein.

One advantage of measuring a plurality of physical characteristics of the driver 210a, 210b is that it increases the reliability and/or sensitivity of the measurement. A change in just a single one of the foregoing parameters can, after all, be attributable to a completely different non-stress-related factor. For example, an elevated skin temperature on the part of the driver 210a, 210b could be the result of a malfunction of the heating system in the cab rather than of the driver 210a, 210b being on the way to an emotional outburst of rage. In the same way, for example, dilated pupils of the driver 210a, 210b may be attributable to an oncoming vehicle having failed to dim its high beams or having poorly adjusted headlights. By measuring a plurality of parameters, such as for example the foregoing, it is possible to filter out at least some possible alternative explanatory models for the deviant physical parameters of the driver, which increases the traffic safety of this method according to these embodiments.

Measurement of the physical characteristic or characteristics of the driver or drivers can be performed continuously, or at certain time intervals according to certain embodiments. The measurements can also be triggered by another party such as another driver, the vehicle owner, medical personnel; or by an event, such as a vehicle start, vehicle stop or the like.

In certain embodiments a starter interlock on the vehicle 220A, 220B is activated when the driver 210A, 210B removes the measuring device 230A, 230B, which interlock is not lifted until the driver 210A, 210B restores the measuring device 230A, 230B.

In certain alternative embodiments, a starter interlock on the vehicle 220A, 220B is activated when the measuring device 230A, 230B detects physical parameters that deviate from the normal parameters for the regular driver by a certain threshold value. It thus becomes possible to prevent a different individual such as an authorized driver or thief from operating the vehicle 220A, 220B.

In certain additional embodiments a starter interlock on the vehicle 220A, 220B in the vehicle convoy 200 is activated when the measuring device 230A, 230B detects physical parameters that differ from the normal parameters for the regular driver by a certain threshold value. This makes it possible to prevent an emotionally agitated driver 210A, 210B from initiating vehicle travel.

Step 402

The stress level of the driver is determined based on the performed measurement.

The determination of the stress level of the driver can be based on the performed measurement, and comprises a comparison between the measured value and a limit value.

For example, the physical parameter that is measured can consist of the pulse of the driver. The measured pulse value of the driver, which can be, for example, 72 beats per minute, can then be compared with a limit value that can be predetermined, or configurable to, for example, 85. The limit value can also be adapted for each individual driver 210A, 210B and be at, for example, 10% above the resting pulse of the driver. When the pulse of the driver in this example falls below the limit value, the driver 210A, 210B can be characterized as harmonious, or unstressed. In such a case the ordinary control algorithm can be used, completely unaffected, to act upon the clutch control system with no adaptation to the parameters of the driver, as the driver 210A, 210B can be considered to be harmonious. However, if on another occasion the pulse of the driver temporarily exceeds 85 beats per minute, the driver 210A, 210B can be categorized as stressed, which can in turn trigger an adaptation of the control algorithm in accordance with the following steps.

One advantage hereof is that the control algorithm is not affected at all when the driver 210A, 210B is unstressed. This makes it possible to maintain the sensitivity of the clutch system for the unstressed driver 210A, 210B while, at the same time, a suppression of driver-dependent parameters can be introduced in the control system 250 for the stressed driver, which yields an improved control system 250.

It should perhaps also be noted that the physical parameter that is measured in other examples can consist of changes in the pulse of the driver. Assume that the pulse of the driver is 72 beats per minute on a first measurement occasion and 85 beats per minute on a second measurement occasion. The pulse increase is then 85−72=13 beats per minute, which value can be compared to a limit value that can be, for example, 7 beats per minute or, for example, 10% of the original value (i.e. of 72). One advantage of measuring changes in the physician parameters of a driver is that it is possible to use the same limit value regardless of which individual driver 210A, 210B is being measured, in certain embodiments.

Furthermore, according to certain additional embodiments, the physical parameter that is measured in yet another example can consist of the change in the pulse of the driver per unit of time. Assume that the pulse of the driver is 72 beats per minute on a first measurement occasion and 85 beats per minute on a second measurement occasion that occurs one minute later. The pulse change per minute is then 85−72=13 beats per minute, which value can be compared to a limit value that can, for example, be 7 beats per minute or, for example, 10% of the original value (i.e. of 72). This embodiment also has the advantage that it is possible to use the same limit value regardless of which individual driver 210A, 210B is being measured, in certain embodiments.

Step 403

The control algorithm is adapted to the determined 402 stress level of the driver.

According to certain embodiments, this adaptation of the control algorithm comprises a reduction of the driver-dependent parameter value in proportion to the determined 402 stress level of the driver.

For example, a measured value for a driver parameter that is lower than a limit value can reduce the driver-dependent parameter value by 0%, a measured value for a driver parameter that equals the limit value can reduce the driver-dependent parameter value by 10%, and a measured value for a driver parameter that exceeds the limit value by 10% can reduce the driver-dependent parameter value by 30%, to name just one arbitrary and non-limiting example.

The adaptation of the control algorithm can, in certain embodiments, comprise a mapping of the determined 402 stress level of the driver against a corresponding reduced parameter value and the insertion of the reduced parameter value into the control algorithm.

It is thereby possible to compare measured values for the measured driver parameter to measured values or a range of measured values in a table and, by means of such mapping, to extract a corresponding reduced parameter value that can then be inserted into the algorithm in order to suppress the request for a shift of gears on the part of the emotional driver and thus enable a gentler transfer of power.

The adaptation of the control algorithm can further comprise the introduction of a time filter, wherein the length of the time delay is in proportion to the determined 402 stress level of the driver.

For example, a measured value for a driver parameter that is below a limit value can result in a non-existent time delay; a measured value for a driver parameter that equals the limit value can result in a time delay of one second, and a measured value for a driver parameter that exceeds the limit value by 10% can result in a time delay of three seconds, just to name one arbitrary and non-limiting example.

In certain embodiments the adaptation of the control algorithm can comprise an expansion of the permissible rpm range within which gear shifting is performed. This expansion can be in proportion to the determined 402 stress level of the driver. A driver parameter that is below a limit value can thus result in a non-existent expansion of the permissible rpm range; a measured value for a driver parameter that equals the limit value can result in an expansion of the permissible rpm range by 10%, and a measured value for a driver parameter that exceeds the limit value by 10% can result in an expansion of the permissible rpm range by 20%, just to name a few examples. Unnecessary gear shifting can thereby be avoided.

In certain embodiments of the method 400, the control algorithm for the vehicle convoy 200 increases the distance between the vehicles 220A, 220B that are included in the vehicle convoy 200 when the determined 402 stress level of the first driver exceeds a limit value. The level of safety is thereby increased in that the risk of a chain collision is reduced.

In certain embodiments, the method 400 comprises the triggering of an emergency stop of the vehicle convoy 200 when the determined 402 stress level of the driver exceeds a limit value. This makes it possible to prevent, for example, an acute illness on the part of the driver 210A of the lead vehicle from having consequences for the forward travel of the vehicle convoy 200. The emergency stop further enables the first driver 210A to receive medical assistance from his colleagues or other individuals at the scene.

In certain embodiments the distance between the vehicles 220A, 220B in the vehicle convoy 200 is increased by, for example, 50% when the determined 402 stress level of the first driver exceeds a first limit value, by 70% when the stress level exceeds a second limit value, by 100% when the stress level exceeds a third limit value, and an emergency stop is activated when the stress level exceeds a fourth limit value. It should be noted that these values are examples.

In certain embodiments of the method 400, the control algorithm for the vehicle convoy 200 comprises measures to send an indication from a stress alarm to other drivers 210B of vehicles 220A, 220B in the vehicle convoy 200 when the determined 402 stress level of the first driver exceeds a limit value.

This makes it possible to prevent, for example, an acute illness on the part of the driver 210A of the lead vehicle from having consequences for the forward travel of the vehicle convoy 200. Other drivers 210B in the vehicle convoy 200, or at least one other driver 210B in the vehicle convoy 200 can thus be warned about the degraded health condition of the lead driver and thereby be enabled to perform, or prepare themselves to perform, first aid measures such as cardiopulmonary resuscitation or the like, should such prove relevant.

Step 404

This method step is performed only in certain alternative embodiments of the method 400.

In certain embodiments of the method 400, the control of the vehicle convoy is turned over to another driver 210B in the vehicle convoy 200 when the first driver 210A is the lead vehicle of the vehicle convoy and the determined 402 stress level of said driver exceeds a limit value.

Step 405

This method step is performed only in certain alternative embodiments of the method 400.

According to these alternative embodiments, the measured 401 physical characteristic of the driver 210A, 210B is sent to an external data storage unit 260 to enable a health analysis of the driver 210A, 210B.

The external storage unit 260 can be disposed, for example, at the vehicle owner, the vehicle manufacturer or another third party actor, and arranged so as to store the physical characteristics of the drivers 210A, 210B or a plurality of drivers along with, for example, chronological and/or geographical positioning information. In addition, the external storage unit 260 can be arranged so as to analyze these stored measured values. This information can then be used to detect a severely degraded health condition on the part of individual drivers 210A, 210B, and professional assistance can then be summoned to arrange for additional measures to halt the negative progression of the driver who is getting sick. In the event of a detected acute illness or potential accident, emergency aid can, in some embodiments, be sent to the vehicle position, and/or medical advice of the first aid type can be provided remotely.

The stored measured values can also be used, for example, to investigate accidents that have occurred, in a manner similar to the "black box" in an airplane. This makes it possible to analyze the stored measured values associated with the detected emotional outbursts of the driver, for example by enabling the detection of which physical parameter(s) or parametric changes preceded an accident. Such detection can be used to further improve the control algorithm for the transmission system 250, as well as other control algorithms, such as those for brake systems or the like.

According to certain embodiments, information about measurement results for each individual driver 210A, 210B of vehicles 220A, 220B in the vehicle convoy 200 is sent to a control system 250 that governs the control of the vehicle convoy 200. The driver 210A of the lead vehicle 220A can thus be warned that another driver 210B of another vehicle 210B in the vehicle convoy 200 has an increased stress level, and take appropriate steps.

Figure 5:
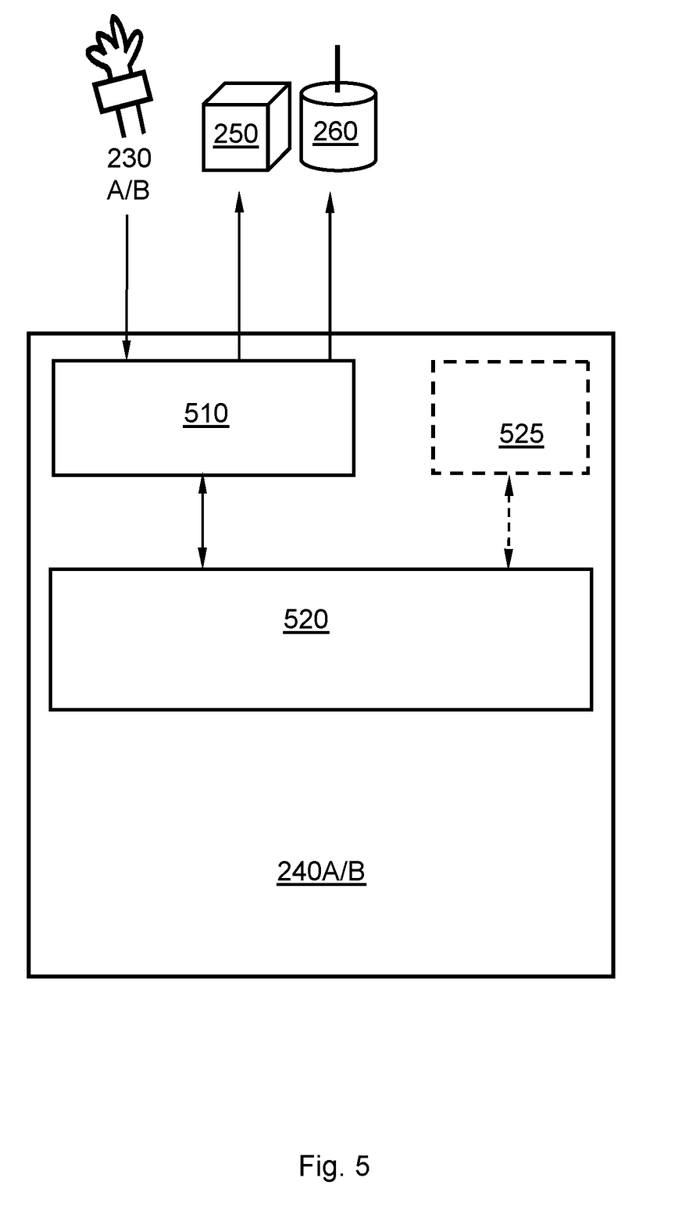
FIG. 5 is an illustration of a control unit for adapting a control algorithm according to one embodiment of the invention.

FIG. 5 illustrates an embodiment of a control unit 240A, 240B for governing the control system 250 of a vehicle convoy by means of an adaptable control algorithm. Said control unit 240A, 240B is configured so as to perform at least certain of the aforedescribed method steps 401-405, included in the description of the method 400 for adapting a control algorithm comprising at least one driver-dependent parameter to the stress level of a driver, which control algorithm governs a control system 250.

The stress level of the driver is determined based on a measured physical characteristic of the driver 210A, 210B comprising at least one of: systolic blood pressure, diastolic blood pressure, pulse, cardiac minute volume, vascular resistance, respiratory volume, respiratory rate, body temperature, skin temperature, blood adrenalin level, blood cortisol level, blood noradrenalin level, transpiration volume, amount of hand sweat exuded, electrical conductivity of the skin, eye movement, dilated nostrils, muscular tension, body movement, speech volume, voice strength and/or pupil size according to various embodiments.

The measured physical characteristic of the driver 210A, 210B can comprise, for example, a level change in at least one measured physical characteristic of the driver 210A, 210B in certain embodiments. The measured physical characteristic of the driver 210A, 210B can further comprise a level change per unit of time in at least one measured physical characteristic of the driver 210A, 210B.

In order to adapt the control algorithm to the stress level of the driver in a correct manner, the control unit 240A, 240B comprises a number of components that are described in detail in the text below. However, it should be noted that certain of the described secondary components occur in certain embodiments. It may further be noted that additional electronics in the control unit 240A, 240B that are not entirely necessary in order to understand the function of the control unit 240A, 240B according to the invention have not been depicted in FIG. 5 in order to avoid making it more difficult to understand the invention.

The control unit 240A, 240B comprises a communication module 510 for receiving a measurement result from a measurement of at least one physical characteristic of the driver 210A, 210B. The measurement result is received over a wireless or wired interface from a measuring unit 230A, 230B. The communication module 510 is, in certain embodiments, further arranged so as to send instructions to a control system 250, which in turn affects the maneuvering of the vehicle convoy. In certain embodiments the communication module 510 is also arranged so as to send measurement data to an external unit 260 for storing and analyzing said measurement data. This communication to the external storage unit 260 is carried out wirelessly.

In certain embodiments the communication module 510 can consist of a separate transmitter and receiver. In certain embodiments the communication module 510 can consist of a transceiver that is adapted so as to transmit and receive radio signals, and wherein parts of the design, for example the antenna, are common to transmitter and receiver. The communication module 510 can further be adapted for wireless information transfer by means of radio waves, WLAN, Bluetooth or an infrared transmitter/receiver module. However, in certain embodiments the communication module 510 can be specially adapted for wireless information exchange with the measuring device 230 and/or the data bus of the vehicle.

The control unit 240A, 240B further comprises a processor circuit 520 arranged so as to determine the stress level of the driver based on the performed measurement, and also arranged so as to adapt the control algorithm to the determined stress level of the driver.

In certain embodiments the processor circuit 520 can be arranged so as to determine the stress level of the driver based on a comparison between the measured value and a limit value.

In certain embodiments the processor circuit 520 can be arranged so as to adapt the control algorithm by reducing the driver-dependent parameter value in proportion to the determined stress level of the driver.

For example, a measured value for a driver parameter that is below a limit value can reduce the driver-dependent parameter value by 0%, a measured value for a driver parameter that equals the limit value can reduce the driver-dependent parameter value by 10%, and a measured value for a driver parameter that exceeds the limit value by 10% can reduce the driver-dependent parameter value by 30%, to name just one arbitrary and non-limiting example.

In certain embodiments the processor circuit 520 can be arranged so as to adapt the control algorithm by mapping the determined stress level of the driver against a corresponding reduced parameter value and inserting said reduced parameter value into the control algorithm.

This makes it possible to compare a measured value for the measured driver parameter to a measured value or range of measured values in a table and, by means of this mapping, to extract a corresponding reduced parameter value that can then be inserted into the control algorithm in order to in order to suppress the request for a shift of gears by the emotional driver and enable a gentler transfer of power.

In certain embodiments the processor circuit 520 can be arranged so as to adapt the control algorithm by inserting a time filter, wherein the length of the time delay is in proportion to the determined stress level of the driver.

For example, a measured value for a driver parameter that is lower than a limit value can result in an non-existent time delay; a measured value for a driver parameter that equals the limit value can result in a time delay of one second, and a measured value for a driver parameter that exceeds the limit value by 10% can result in a time delay of three seconds, just to mention one arbitrary and non-limiting example.

The processor circuit 520 can consist, for example, of one or a plurality of a Central Processing Unit (CPU), microprocessor or other logic designed so as to interpret and execute instructions and/or to read and write data. The processor circuit 520 can process data for inflows, outflows or the data processing of data that also comprises buffering of data, control functions and the like.

In certain alternative embodiments the control unit 240A, 240B comprises a memory unit 52, which constitutes a storage medium for data. The memory unit 525 can consist, for example, of a memory card, flash memory, USB memory, hard drive or other similar data storage unit, such as any of the group comprising ROM (Read-Only Memory), PROM (Programmable Read-Only Memory), EPROM (Erasable PROM), Flash memory, EEPROM (Electrically Erasable PROM), etc in various embodiments.

The invention further comprises a computer program for adapting a control algorithm comprising at least one driver-dependent parameter, wherein the control algorithm governs a control system 250. The computer program is arranged so as to perform the method 400 according to at least one of the previously described method steps 401-405 when the computer program is executed in a processor circuit 520 in the control unit 240A, 240B.

The method steps 401-405 for adapting a control algorithm to the stress level of a driver can be implemented by means of one or a plurality of processor circuits 520 in the control unit 240A, 240B together with computer program code for performing one, several, certain or all of the method steps 401-405 that are described above. A computer program can thereby include instructions for performing the method steps 401-405 when the computer program is loaded into the processor circuit 520.

Figure 6:
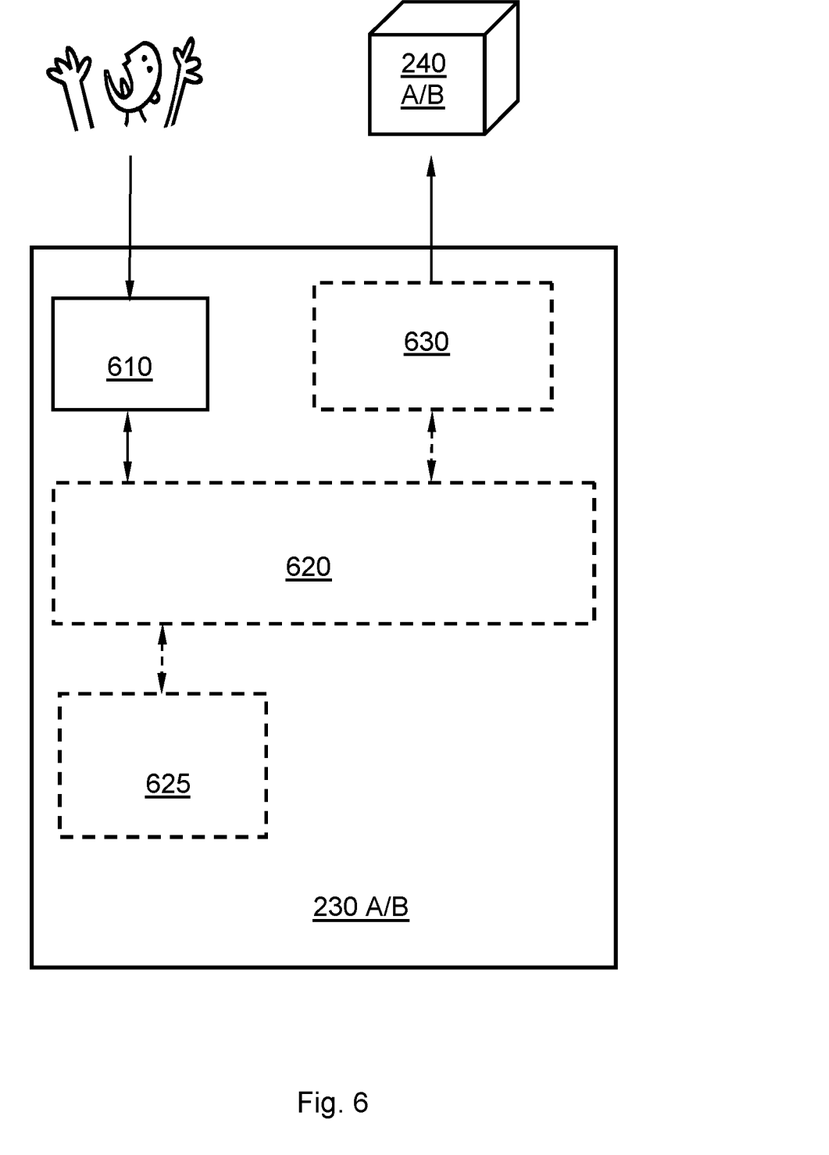
FIG. 6 is an illustration of a measuring device according to one embodiment of the invention.

FIG. 6 shows a measuring device 230A, 230B. The measuring device 230A, 230B is arranged so as to supply measurement results for adapting a control algorithm comprising at least one driver-dependent parameter, wherein the control algorithm governs a control system 250 for a vehicle convoy 200.

The measuring device 230A, 230B can comprise or at least partly consist of a blood pressure meter, pulse meter, moisture meter, thermometer, motion detector, microphone, voice analysis device, horn, mobile phone, portable computer, laptop computer, tablet computer, network computer, handheld computer or the like.

In order to provide measurement results for at least one driver-dependent physical parameter in a correct manner, the measuring device 230 comprises a number of components that are described in detail in the text below. It must however be noted that certain of the described secondary components occur in certain embodiments. It may further be noted that additional electronics in the measuring device 230A, 230B, which are not entirely necessary to understand the function of the measuring device 230A, 230B according to the invention, have not been depicted in FIG. 6 in order to avoid making it more difficult to understand the invention.

The measuring device 230A, 230B comprises a detector 610 for measuring at least one physical characteristic of the driver 210A, 210B.

The detector 610 is further arranged so as to measure at least one of the following physical characteristics of the driver 210a, 210B: systolic blood pressure, diastolic blood pressure, pulse, cardiac minute volume, vascular resistance, respiratory volume, respiratory rate, body temperature, skin temperature, blood adrenalin level, blood cortisol level, blood noradrenalin level, transpiration volume, amount of hand sweat exuded, electrical conductivity of the skin, eye movement, dilated nostrils, muscular tension, body movement, speech volume, voice strength and/or pupil size.

In certain embodiments the measuring device 230A, 230B can comprise a number of detectors 610, which are adapted so as to measure various physical characteristics of the driver 210A, 210B, i.e. of the characteristics enumerated above. Said detectors 610 can be disposed in a plurality of locations in the cab and/or on the driver 210A, 210B. To name one example, the vehicle steering wheel can contain a moisture detector, thermometer and/or measuring elements for electrical conductivity.

One advantage of measuring a plurality of physical characteristics of the driver 210A, 210B is that the reliability and/or sensitivity of the measurement increases. A change in a single one of the foregoing parameters can, of course, have a completely different non-stress-related cause in and of itself. For example, an elevated skin temperature on the part of the driver 210A, 210B could be the result of a malfunction of the heating system in the cab rather than of the driver 210A, 210B being on the way to an emotional outburst of rage. In the same way, for example, dilated pupils of the driver 210A, 210B may be attributable to an oncoming vehicle having failed to dim its high beams or having poorly adjusted headlights.

The measuring device 230A, 230B also comprises a communication module 630 arranged so as to communicate the measured value to a control unit 240A, 240B. The communication module 630 is in turn arranged so as to communicate the measured value wirelessly or via cable to the control unit 240A, 240B and/or a data storage unit 260, in certain embodiments.

In certain embodiments the communication module 630 can consist of a separate transmitter and receiver. In certain embodiments the communication module 630 can consist of a transceiver that is adapted so as to transmit and receive radio signals, and wherein parts of the design, for example the antenna, are common to transmitter and receiver. The communication module 630 can further be adapted for wireless information transfer by means of radio waves, WLAN, Bluetooth or an infrared transmitter/receiver module. However, in certain embodiments the communication module 630 can be specially adapted for wireless information exchange with the control unit 240A, 240B and/or the data bus of the vehicle.

In certain embodiments the measuring device 230A, 230B is designed as a cuff, connectable to the arm or another body part of the driver. This makes it possible to measure, for example, the blood pressure, pulse, skin temperature, dermal electrical conductivity and/or transpiration volume of the driver easily and reliably.

In one embodiment the vehicle 220A, 220B cannot be started unless the driver 210A, 210B is wearing the measuring device 230A, 230B.

In certain embodiments the measuring device 230A, 230B is arranged so as to detect a level change in at least one measured physical characteristic of the driver 210A, 210B. The measuring device 230A, 230B can alternatively be adapted so as to detect a level change per unit of time in at least one measured physical characteristic of the driver 210A, 210B.

Certain embodiments of the invention further comprise a system for adapting a control algorithm comprising at least one driver-dependent parameter, which control algorithm governs a control system 250 of a vehicle convoy 200. Said system comprises a measuring device 230A, 230B according to any of the embodiments described in connection with the presentation in FIG. 6. The system also comprises a control unit 240A, 240B according to any of the embodiments described in connection with the presentation in FIG. 5, which control unit is adapted so as to determine the stress level of the driver based on the performed measurement, and to adapt a control algorithm to the determined stress level of the driver.

Some embodiments of the invention further include a vehicle 220A, 220B that comprises the aforedescribed system 200.

Certain embodiments of the invention further include a vehicle convoy 200 that comprises at least two of the aforedescribed vehicles 220A, 220B.

According to certain alternative embodiments the vehicle 220A, 220B also comprises or is connectable to a unit for determining geographical position, such as a GPS module. This alternative unit is specially adapted so as to determine the present position of the vehicle and enables, for example, storage or marking in order to mark the location of a stress incident on the part of the driver 210A, 210B, optionally together with a time as well. The geographical positions and/or times of stress reactions on the part of the driver 210A, 210B and/or a plurality of drivers can thereby be sent to and stored in the external data storage unit 260 for subsequent display. For example, a stress map can be drawn up based on this collected information, which map can be used in planning travel routes, or to warn the driver(s) 210A, 210B that he/she/they are passing into a high-stress area, based on its geographical position/direction of position change. Harmful stress situations can thereby be eliminated or at least mitigated.

According to certain alternative embodiments, feedback can be provided to the driver 210A, 210B in the event that an elevated stress level is detected on the part of the driver 210A, 210B in order to calm him. Such feedback can consist, for example of the playing of peaceful/relaxing music, an increase in the ventilation/air conditioning of the driver compartment with a view to reducing the temperature and increasing the oxygen supply, or the activation of a massage module built into the driver seat, which can have a pacifying effect on the mentally distraught driver 210A, 210B. The risk of stress-related injuries and/or potential accidents can be further reduced thereby.

It can further be shown that embodiments of the invention are applicable both during gear shifting for forward travel and gear shifting for backing the vehicle convoy 200. However, it may be advantageous in certain cases to activate the foregoing method only in connection with travel in the forward direction of the vehicle convoy in order to reduce the risk of triggering additional driver aggression in connection with backing or parallel parking. Furthermore, in certain embodiments the function according to the invention can be turned off selectively in connection with certain maneuvers, such as during, for example, the forward travel of the vehicle convoy 200 in a shunting mode/maneuvering mode wherein the driver 210A, 210B often drives the vehicle convoy 200 at a very low velocity when, for example, approaching a loading dock or ferry.

The invention according to certain foregoing embodiments has further been exemplified for a situation in which the driver 210a, 210b requests propulsive power via a driver-controllable acceleration element such as a gas pedal. The invention is, however, also applicable in cases where the driver 210a, 210b requests propulsive power in another way, such as by means of some driver-assistance system or other applicable control unit.

It can further be shown that the present invention can be used both in connection with pedal operation, i.e. wherein the driver 210A, 210B himself regulates the requests for engine torque, and in connection with driving with cruise control. The term pedal operation refers here and in this document to essentially all types of regulation adapted so as to regulate requests for torque, such as for example a gas pedal or manual accelerator device.

What is claimed is:

1. A method for governing control of a vehicle convoy, the convoy comprising at least a first vehicle with a first driver and a second vehicle with a second driver, the method for governing including:
    measuring at least one physical characteristic of the first driver indicative of or related to stress of the first driver;
    determining automatically, by a data processor circuit, a stress level of the first driver based on the measured characteristic of the first driver;
    adjusting automatically, by the data processor circuit, the control algorithm based on the determined stress level of the first driver, and the control algorithm for the vehicle convoy sending an indication of a stress alarm to other drivers, including the second driver, of vehicles in the vehicle convoy when the determined stress level of the first driver exceeds a respective selected limit value for the stress level; and
    controlling automatically, by the data processor circuit, the vehicle convoy according to the adjusted control algorithm.

2. The method according to claim 1, wherein the measured physical characteristic of the first driver comprises at least one of: systolic blood pressure, diastolic blood pressure, pulse, cardiac minute volume, vascular resistance, respiratory volume, respiratory rate, body temperature, skin temperature, blood adrenalin level, blood cortisol level, blood noradrenalin level, transpiration volume, amount of hand sweat exuded, electrical conductivity of the skin, eye movement, dilated nostrils, muscular tension, body movement, speech volume, voice strength and pupil size.

3. The method according to claim 2, wherein the measured physical characteristic of the first driver comprises at least one of a level change and a level change per unit of time in at least one measured physical characteristic of the first driver.

4. The method according to claim 1, wherein the determining of the stress level of the first driver based on the measuring of at the least one physical characteristic comprises a comparison between the measured value and a respective limit value of the characteristic.

5. The method according to claim 1, wherein the adjusting of the control algorithm comprises reducing a value of the physical characteristic of the first driver proportionally to the determined stress level of the first driver.

6. The method according to claim 5, wherein the adjusting of the control algorithm comprises mapping the determined stress level of the first driver against a corresponding reduced vehicle-controlling parameter value and inputting the reduced vehicle-controlling parameter value into the control algorithm.

7. The method according to claim 1, wherein the adjusting of the control algorithm comprises inserting a time filter, so that a length of a time delay in adjusting the control algorithm is proportional to the determined stress level of the first driver.

8. The method according to claim 1, wherein the measuring of the at least one physical characteristic of the first driver is performed by a measuring device configured to be connectable to a body part of the first driver.

9. The method according to claim 1, further comprising when the first driver is the first driver of a lead vehicle of the vehicle convoy and is determined to have a stress level which exceeds the limit value:
    transferring control of the vehicle convoy to another driver in the vehicle convoy.

10. The method according to claim 1, wherein the control algorithm for the vehicle convoy is configured to trigger an emergency stop of the vehicle convoy when the determined stress level of the first driver exceeds the limit value.

11. The method according to claim 1, wherein the control algorithm for the vehicle convoy is configured to increase a distance between the vehicles in the vehicle convoy when the determined stress level of the first driver exceeds the limit value.

12. The method according to claim 1, further comprising:
sending information about measurement results for each individual driver of each vehicle in the vehicle convoy to at least one of a control system governing the control of the vehicle convoy and an external data storage unit in order to enable health analyses of the drivers in the vehicle convoy.

13. The method according to claim 1, wherein the control algorithm is adjusted by at least one of:
a vehicle-controlling driver-dependent parameter comprising at least one of the following: inclination of a gas pedal, inclination of a shift pedal, inclination of a brake pedal, change in inclination of the gas pedal, change in inclination of the shift pedal, change in inclination of the brake pedal, change in inclination of the gas pedal per unit of time, change in inclination of the shift pedal per unit of time, change in inclination of the brake pedal per unit of time, steering wheel deflection, and rate of change of steering wheel deflection; and
a driver-independent parameter selected from at least one of the following: vehicle type, inclination of the vehicle, vehicle weight, comfort level, and engine rpm.

14. A non-transitory computer readable medium incorporating a program of instructions configured to a control, when executed by a processor circuit, a vehicle according to the method of claim 1.

15. A control unit for governing the control of a vehicle convoy comprising at least a first vehicle with a first driver and a second vehicle with a second driver the control unit configured to execute an adaptable control algorithm, the control unit comprising:
a communication module configured to receive a measurement result from a measurement of at least one physical characteristic of the first driver;
a processor circuit configured to determine, automatically, a stress level of the first driver based on the measurement, and also configured to adapt the control algorithm to the determined stress level of the first driver and send an indication of a stress alarm to other drivers of vehicles in the vehicle convoy when the determined stress level of the first driver exceeds a limit value; and
the processor circuit configured to control, automatically, the vehicle convoy according to the adapted control algorithm.

16. The control unit according to claim 15, wherein the measured physical characteristic of the first driver comprises at least one of: systolic blood pressure, diastolic blood pressure, pulse, cardiac minute volume, vascular resistance, respiratory volume, respiratory rate, body temperature, skin temperature, blood adrenalin level, blood cortisol level, blood noradrenalin level, transpiration volume, amount of hand sweat exuded, electrical conductivity of the skin, eye movement, dilated nostrils, muscular tension, body movement, speech volume, voice strength and pupil size.

17. The control unit according to claim 15, wherein the measured physical characteristic of the first driver comprises at least one of a level change and a level change per unit of time, in at least one measured physical characteristic of the first driver.

18. The control unit according to claim 15, wherein the processor circuit is configured to determine the stress level of the first driver based on a comparison between the measured value and the limit value.

19. The control unit according to claim 15, wherein the processor circuit is configured to reduce or adjust a driver-dependent parameter value in proportion to the determined stress level of the first driver.

20. The control unit according to claim 15, wherein the processor circuit is configured to map the determined stress level of the first driver against a corresponding reduced parameter value and insert the reduced parameter value into the control algorithm.

21. The control unit according to claim 15, wherein the processor circuit is configured to insert a time filter, configured so that a length of a time delay in sending a stress measurement is proportional to the determined stress level of the first driver.

22. A system for governing a vehicle convoy, the convoy comprising at least a first vehicle with a first driver and a second vehicle with a second driver,
the system comprising:
a measuring device comprising a detector configured for measuring at least one physical characteristic indicative of or related to stress of the first driver;
a communication module configured to communicate a value of the measured physical characteristic to a control unit;
the control unit configured to determine, automatically, a stress level of the first driver based on the performed measurement, and to adapt the control algorithm to the determined stress level of the first driver and further to send an indication of a stress alarm to other drivers of vehicles in the vehicle convoy when the determined stress level of the first driver exceeds a limit value; and
the control unit configured controlling automatically the vehicle convoy according to the adapted control algorithm.

23. A vehicle comprising a system according to claim 22.

24. A vehicle convoy comprising at least two of the vehicles according to claim 23.

25. The method according to claim 1, wherein the control algorithm of the vehicle convoy affects and guides decisions regarding at least one of maneuvering, velocity regulation, gear shifting and vehicle spacing of the vehicle convoy.

26. The method according to claim 1, further comprising activating a starter interlock on the first vehicle when the measured physical characteristic of the first driver differs by a selected threshold value from a normal measure of the physical characteristic for the first driver.

* * * * *